United States Patent [19]

Hawman et al.

[11] Patent Number: 4,670,657

[45] Date of Patent: Jun. 2, 1987

[54] ASTIGMATIC COLLIMATOR

[75] Inventors: Eric G. Hawman, Buffalo Grove; Jiang Hsieh, Des Plaines, both of Ill.

[73] Assignee: Siemens Gammasonics, Inc., Des Plaines, Ill.

[21] Appl. No.: 717,635

[22] Filed: Mar. 29, 1985

[51] Int. Cl.$^4$ .............................................. G01T 1/166
[52] U.S. Cl. ............................... 250/505.1; 250/363 S
[58] Field of Search .................. 378/149; 250/363 SB, 250/363 SC, 363 SF, 363 SR, 505.1, 363 SH

[56] References Cited

U.S. PATENT DOCUMENTS

| | | | |
|---|---|---|---|
| 4,081,687 | 3/1978 | York et al. | 378/149 |
| 4,181,839 | 1/1980 | Hatton et al. | 378/148 |
| 4,250,392 | 2/1981 | Leask et al. | 250/505.1 |
| 4,584,478 | 4/1986 | Genna et al. | 250/363 S |

Primary Examiner—Janice A. Howell
Assistant Examiner—Constantine Hannaher
Attorney, Agent, or Firm—Mark H. Jay

[57] ABSTRACT

A collimator collimates radiation so that each beam passes through two focal lines. One of the lines is in a transaxial plane and the other line is in an axial plane. The focal length in the transaxial plane is longer than is the focal length in the axial plane. In the preferred embodiment, the focal lines are perpendicular, whereby an anamorphic collimator is produced. Alternatively, the focal lines are nonparallel, producing an astigmatic collimator.

7 Claims, 9 Drawing Figures

ASTIGMATIC COLLIMATOR

BACKGROUND OF THE INVENTION

The invention relates to collimators, and more particularly relates to fucussing collimators for use in single photon emission computerized tomography, or SPECT. In its most particular sense, the invention relates to focussing collimators for use in SPECT examinations of distal body parts such as the head.

As a gamma camera is brought closer to a body organ to be imaged, the quality of the image generally improves. This occurs because the resolution of the system improves as the distance to the collimator decreases.

A conventional collimator used in transaxial rotational camera SPECT is parallel to the axis of rotation. In cranial examinations, this arrangement produces a relatively wide gap between the top of the brain and the sensitive crystal surface, and a corresponding reduction in resolution there.

One object of the invention is to provide a collimator which can reduce, on an overall basis, the gap between the sensitive crystal surface and a distal body part such as a patient's head, with consequential improvement in system resolution.

Another object is to generally improve the sensitivity of cameras used for SPECT examinations and to reduce data acquisition time.

A further object is to improve on existing cranial scanning technique and apparatus.

Yet another object is to generally improve on the prior art.

SUMMARY OF THE INVENTION

In accordance with the invention, there is provided an astigmatic collimator, i.e. a collimator which focuses to more than one point, i.e. has at least two focal lines. Advantageously, and in a preferred embodiment, the collimator has one direction of focus in an axial SPECT plane and another direction of focus in a transaxial SPECT plane. Still further advantageously, the focal length in the axial plane is shorter than the focal length in the transaxial plane. This results is an anomorphic callimator.

In use, the crystal is inclined with respect to its axis of rotation about the patient's body so that, on an overall basis, the distance between the brain and the sensitive surface of the crystal is minimized, enabling sensitivity and resolution to be optimized.

To make the invention practical for use, there is disclosed a preferred reconstruction procedure which permits image reconstruction to be carried out using the same computer resources now in use in conventional SPECT examinations.

The invention will be better understood with reference to the following drawings and the detailed description of preferred embodiments.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
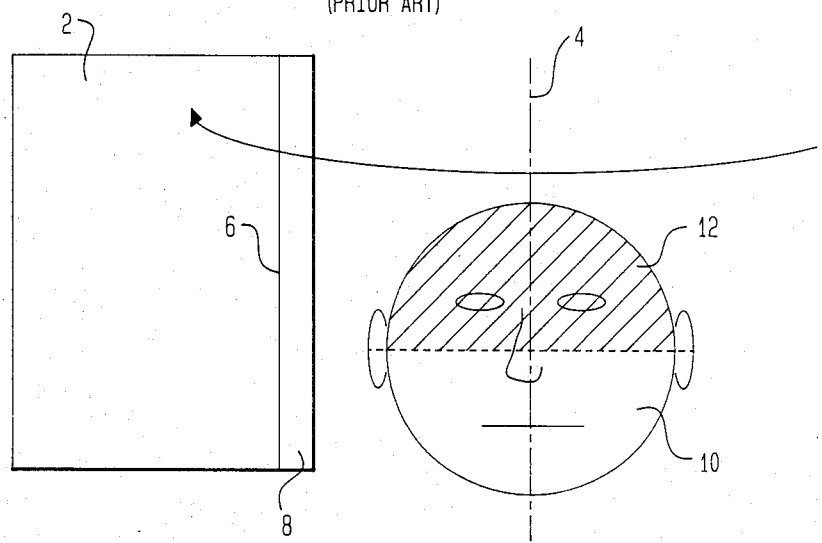
FIG. 1 illustrates conventional rotational camera transaxial SPECT cranial scanning.
Figure 2:
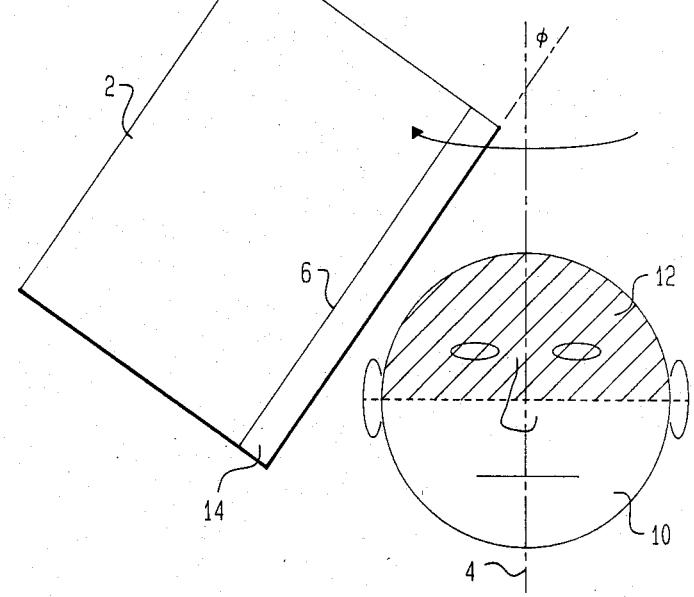
FIG. 2 illustrates the preferred embodiment of the invention utilized for rotational camera transaxial SPECT cranial scanning.

In rotational camera transaxial SPECT, a camera generally indicated by reference numeral 2 is rotated about an axis 4. The sensitive crystal surface 6 of the camera 2 is parallel to the axis 4, and a collimator 8 is attached to the camera 2 so that, e.g. gamma radiation from a patient 10 and more particularly the patient's brain 12 is collimated to form an image on the sensitive crystal surface 6.

In this known arrangement, there is a comparatively wide variation of the gap between the patient's brain 12 and the sensitive surface 6; there is for example a much wider gap at the top of the patient's head than at ear level. It is advantageous to reduce this gap on an overall basis, and not just at a single point, i.e. the ear.

In accordance with the preferred embodiment described below, the camera 2 is still rotated about the axis 4, but the sensitive crystal surface 6 is inclined at an angle $\phi$ with respect to the axis 4. The preferred embodiment, generally indicated by reference numeral 14, is attached to the camera 2 so as to collimate radiation coming from the brain 12 and thereby form an image on the sensitive crystal surface 6.

In accordance with this preferred embodiment 14, the angle $\phi$ is 25° and the distance between the center of the patient's head and the surface of the preferred embodiment 14 is nominally 14 centimeters. This increases sensivity and resolution on an overall basis because there is less variation in the gap between the brain 12 and the sensitive crystal surface 6.

Figure 3:
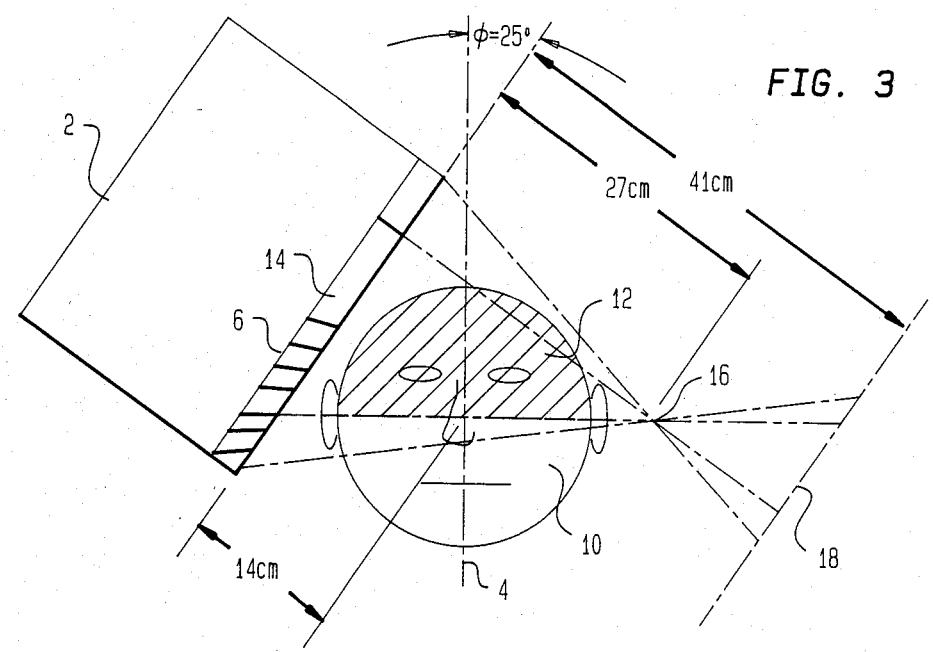
FIG. 3 schematically illustrates how the preferred embodiment focusses.

The focussing scheme of the preferred embodiment 14 will now be explained with reference to FIG. 3. The preferred embodiment 14 focuses along a line of vertical focus 16 and a line of horizontal focus 18. This creates a five-surfaced volume 20 of focus which is bounded by the preferred embodiment 14, the two extreme planes of horizontal focus, and the two extreme planes of vertical focus. The focal length in all axial planes (i.e. the distance between the sensitive crystal surface 6 and the line of vertical focus 16) is preferably 27 centimeters. The focal length in all transaxial planes (i.e. the distance between the sensitive crystal surface 6 and the line of horizontal focus 18) is preferably 41 centimenters. When three dimensions are used, the volume of focus 20 of the preferred embodiment 14 encompasses the entire brain 12 and little else. Because the collimator has different focal lengths (and therefore different magnifications) along mutually perpendicular directions, the collimator is anamorphic. This makes the most productive use of the sensitive crystal surface 6.

Figure 7:
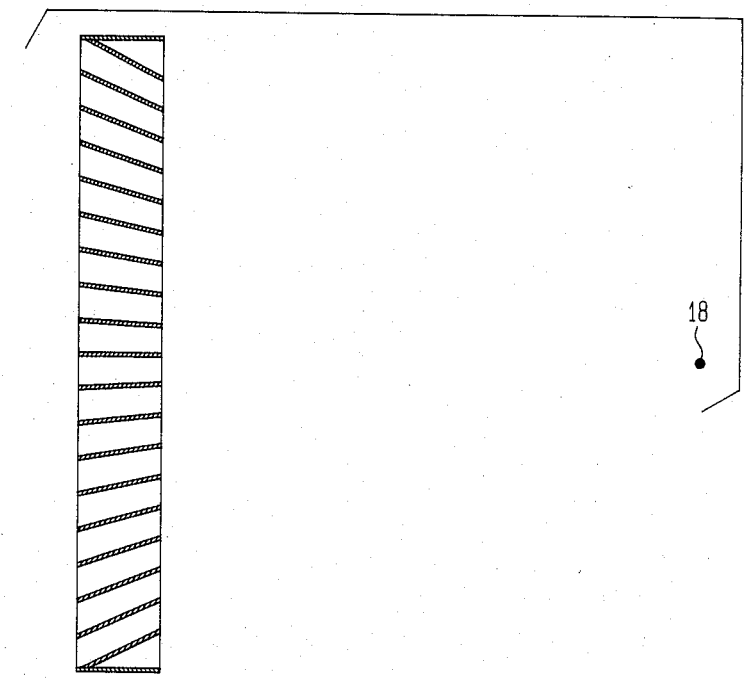
FIG. 7 is an enlarged schematic illustration of how the preferred embodiment focuses along a line of horizontal focus.
Figure 8:
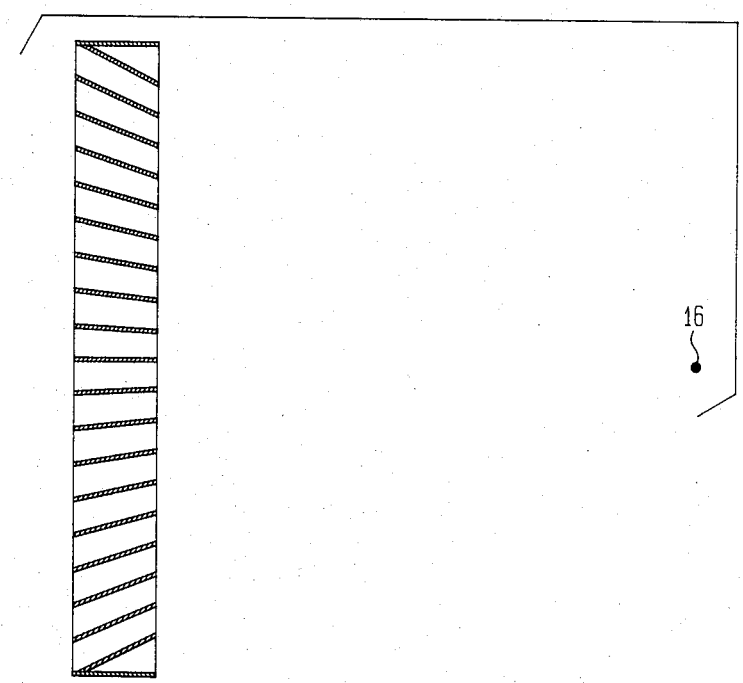
FIG. 8 is an enlarged schematic illustration of how the preferred embodiment focuses along a line of vertical focus.

The preferred embodiment 14 can be made using conventional lead-foil techniques, or alternatively by casting. The septa in the preferred embodiment 14 are directed in such a manner that each collimated beam passes through two focal lines: the line of vertical focus 16 and the line of horizontal focus 18. This is shown in an enlarged and schematic manner in FIGS. 7 and 8.

The preferred reconstruction technique for use with the preferred embodiment will now be explained with reference to FIGS. 4-6.

Figure 4:
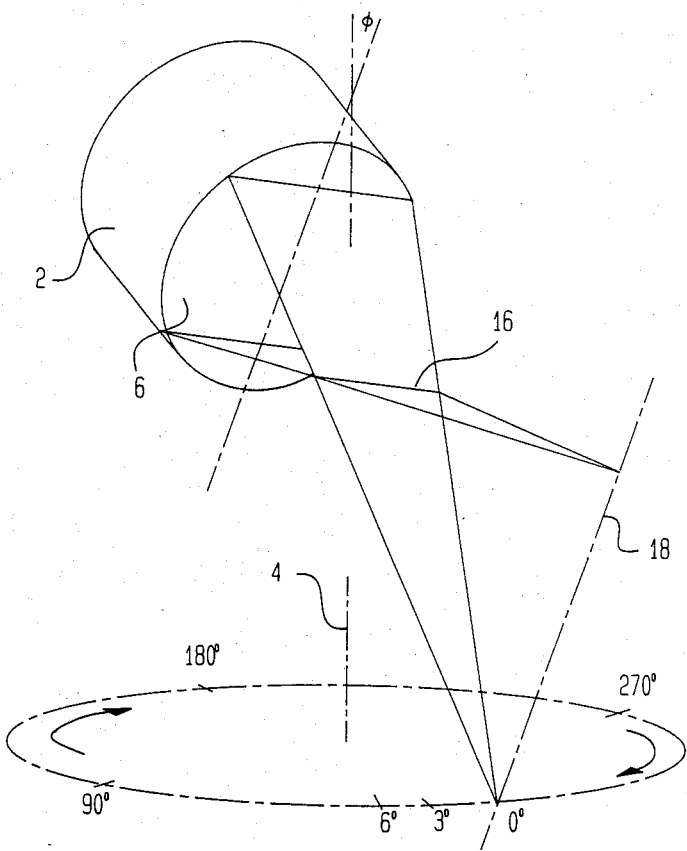
FIG. 4 illustrates the relationship between image frames taken during data acquisition using the preferred embodiment.
Figure 3A:
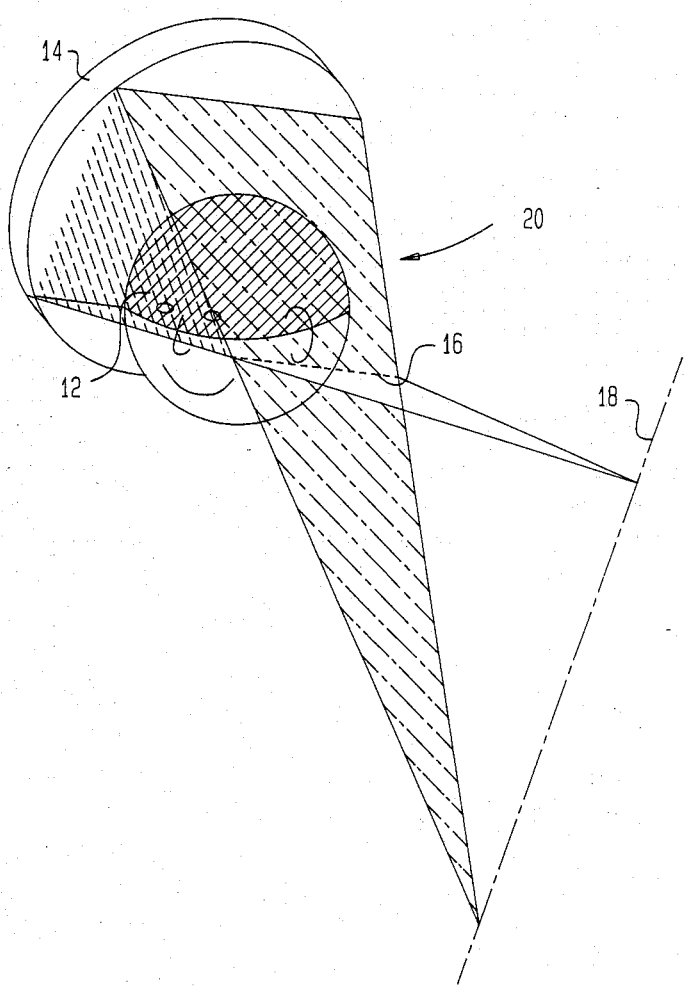
FIG. 3A schematically illustrates how the region of focus of the preferred embodiment encompasses a subject's brain.

In FIG. 4, the preferred embodiment 14 is shown positioned at the first image frame of the data acquisition process. After that image fram has been acquired (i.e. after the intensities of all the points on the sensitive crystal surface 6 have been recorded), the collimator 14 is rotated by, e.g. 3° about the axis 4. After this second image frame has been recorded, the collimator 14 is advanced once more, and this process is repeated until the collimator 14 has been rotated by a full 360°. In this example, there are 120 image frames for each 360° rotation of the camera, but this is not a part of the invention and there may be more or fewer image frames.

The information thus acquired represents, e.g. 120 images of the brian as viewed from 120 rotation angles. Image data for each view can be assigned to a local coordinate system corresponding to the view angle and slice number, i.e. to a specific fan beam slice 22 (FIG. 5). Local coordinate systems for each view and slice are denoted by $X_1$, $Y_1$, $Z_1$; $X_2$, $Y_2$, $Z_2$, etc. During the reconstruction process, all of these images are mapped into a central fixed coordinate system X, Y, Z. This is preferably carried out using a reconstruction procedure described in connection with FIG. 6.

In accordance with this procedure, the final image is reconstructed image frame by image frame, and slice by slice within each image frame. The first image is read into the processing computer, and each pixel in that image is normalized. In this example, the normalization is carried out by dividing the intensity of the pixel in question by the distance between that pixel and the origin of the corresponding local coordinate system, and repeating the process until all pixels have been normalized.

Figure 5:
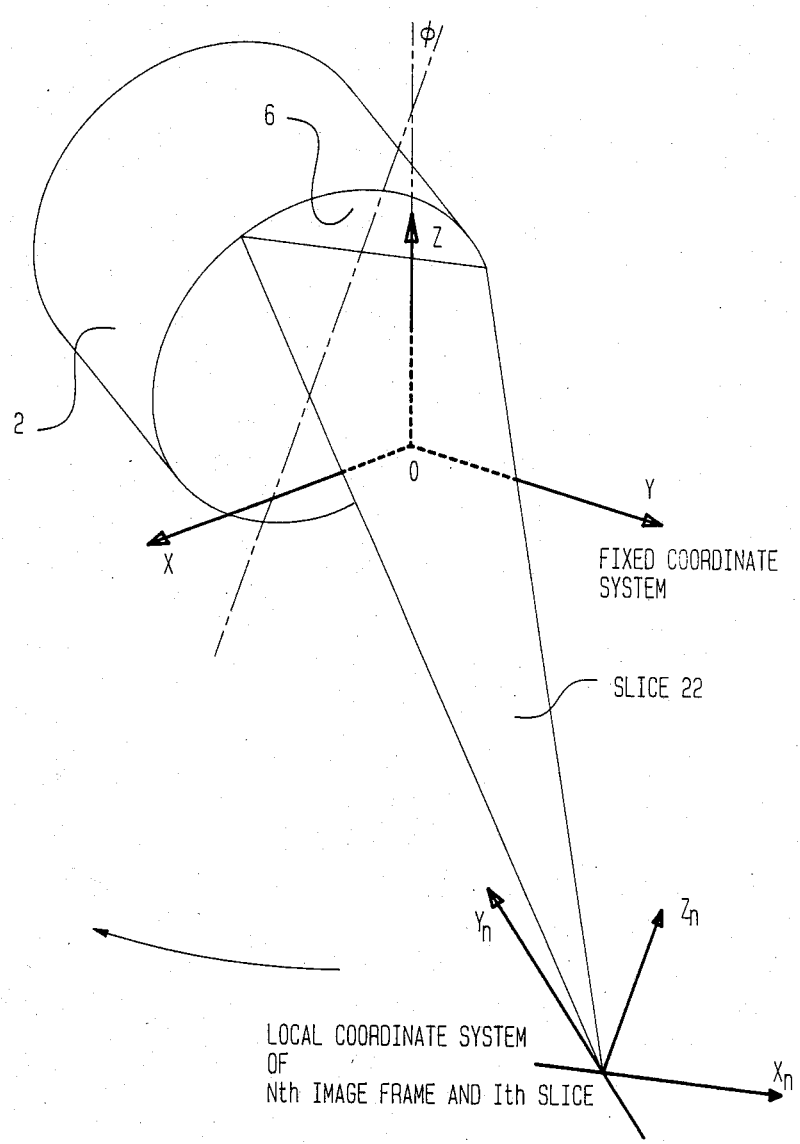
FIG. 5 illustrates the relationship between the fixed and local coordinate systems associated respectively with a patient's head and the moving collimator.
Figure 6:
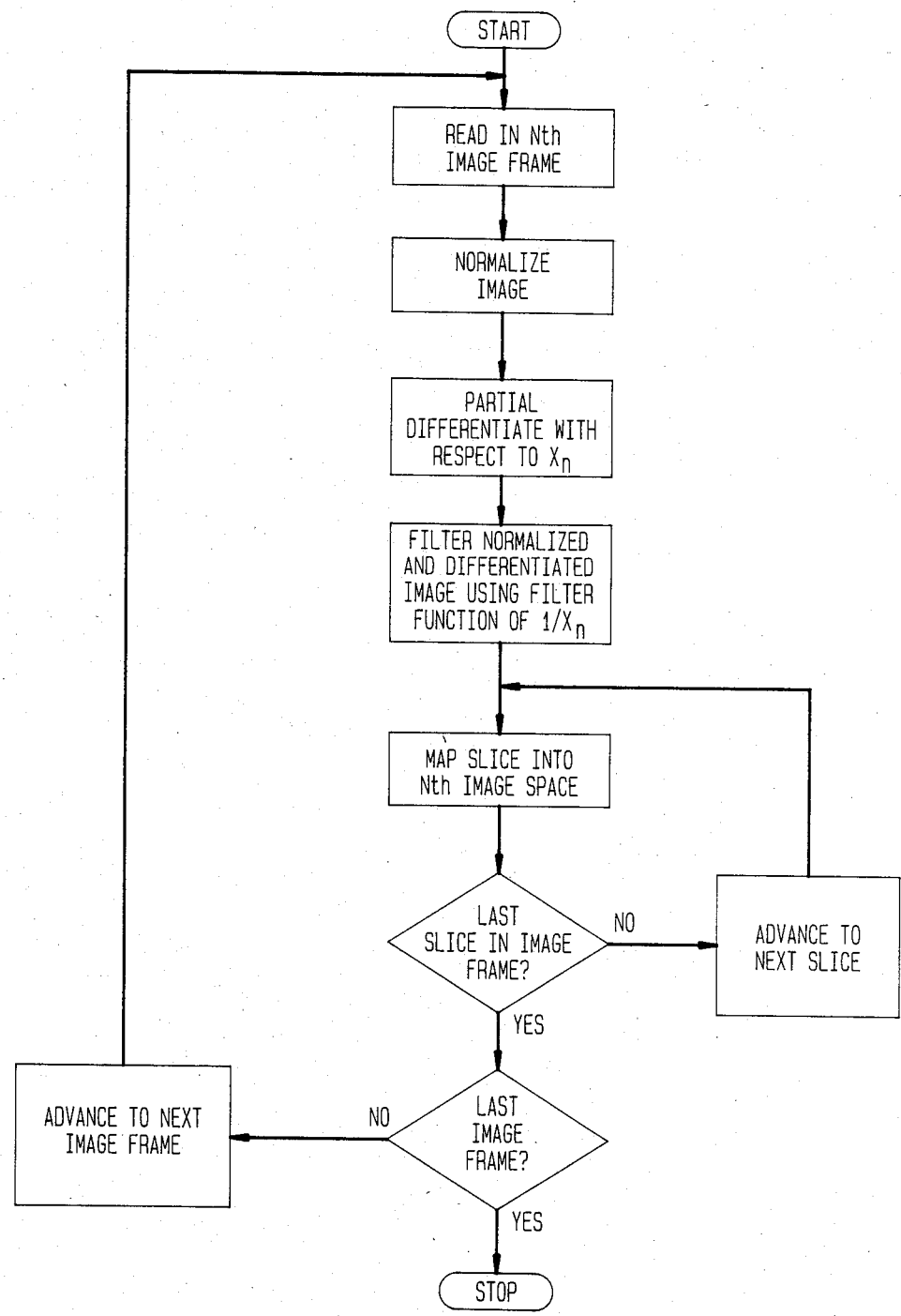
FIG. 6 is a flow chart illustrating the preferred reconstruction procedure for use with the preferred embodiment.

Next, each slice of the image frame (i.e. each line of pixels extending in the $X_n$ direction, one such line is being shown in FIG. 5) is partially differentiated with respect to $X_n$ and then filtered using a filter function of $1/X_n$. Put another way, there is formed from the normalized image $g_n'$ a filtered and convolved image $g_n''$ according to the relationship $$g_n'' = \frac{1}{X_n} * \frac{\partial}{\partial X_n} g_n' \qquad (1)$$

$$g_n'' = \int_{-\infty}^{\infty} \frac{1}{(X_n - l)} \cdot \frac{\partial}{\partial l} g_n' dl \qquad (2)$$

After filter convolution, each slice is backprojected one after the other into the fixed central coordinate system X, Y, Z until all of the slices in the image frame have been backprojected. Put another way, there is successively built up in the fixed central coordinate system X, Y, Z a three dimensional image f. The image $f_n$ is derived from the relationship $$f_n = \eta^2 g_n'' \qquad (3)$$

where $\eta$ is the magnification factor equal to the horizontal focal length divided by $Y_n$.

A transformation matrix $T_n$ represents the transformation between the nth local coordinate system $X_n$, $Y_n$, $Z_n$ and the fixed coordinate system X, Y, Z. Since there are 120 image frames in this example, the reconstructed image f comes from the relationship.

$$f = \sum_{n=1}^{120} f_n \cdot T_n \qquad (4)$$

After all slices in the image have been so backprojected, the next image frame is processed, until all 120 image frames have been nomalized, differentiated, filtered, and backprojected. At this point, the image reconstruction process is finished.

The invention does not reside in the particular constrution procedure utilized nor in the alogrithms used in that procedure. These are only exemplary, and others may be used instead.

Those skilled in the art will understand that changes can be made in the preferred embodiment here described, and that this embodiment can be used for other purposes. Such changes and uses are within the scope of the invention, which is limited only by the claims which follow.

What is claimed is:
1. An astigmatic collimator.
2. The collimator of claim 1, wherein the collimator has two directions of focus.
3. The collimator of claim 2, wherein said directions are mutually perpendicular.
4. The collimator of claim 3, wherein one of said directions is in an axial plane when the collimator is used in SPECT and another of said directions is in a transaxial plane when the collimator is used in SPECT, and wherein the focal length in said axial plane is shorter than the focal length in said transaxial plane.
5. The collimator of claim 1, wherein the collimatro is of a type which collimator non-visible radiation.
6. An astigmatic collimator for use in SPECT cranial examinations, comprising a radiation-absorbing material arranged to have a first focal length in an axial SPECT plane and a second focal length in a transaxial SPECT plane, said first focal length being shorter than said second focal length.
7. An anamorphic collimator.

* * * * *

UNITED STATES PATENT AND TRADEMARK OFFICE
CERTIFICATE OF CORRECTION

PATENT NO. : 4,670,657

DATED : June 2, 1987

INVENTOR(S) : HAWMAN, et al.

It is certified that error appears in the above-identified patent and that said Letters Patent is hereby corrected as shown below:

```
Column 1, line 7:   change "fucussing" to --focussing--;
Column 1, line 44:  change "is" to --in--;
Column 1, line 45:  change "callimator" to --collimator--.
Column 2, line 49:  "14" (second occurrence) should be in a standard typeface,
                    not a bold typeface;
Column 2, line 50:  change "sensivity" to --sensitivity--;
Column 2, line 65:  "41" should be in a standard typeface, not a bold typeface.
Column 3, line 18:  change "fram" to --frame--.
Column 4, formula (2);  The integral sign ∫ is missing between the limits of
                    negative and positive infinity.
Claim 5, line 1: change "collimatro" to --collimator--.
Claim 5, line 2:  change "collimator" to --collimates--.
```

Signed and Sealed this

Fifteenth Day of March, 1988

*Attest:*

DONALD J. QUIGG

*Attesting Officer*   *Commissioner of Patents and Trademarks*